United States Patent
Galea

(10) Patent No.: US 7,905,920 B2
(45) Date of Patent: Mar. 15, 2011

(54) SUPPORT SYSTEM FOR INTERVERTEBRAL FUSION

(75) Inventor: Anna M. Galea, Waltham, MA (US)

(73) Assignee: Foster-Miller, Inc., Waltham, MA (US)

( * ) Notice: Subject to any disclaimer, the term of this patent is extended or adjusted under 35 U.S.C. 154(b) by 191 days.

(21) Appl. No.: 11/207,371

(22) Filed: Aug. 19, 2005

(65) Prior Publication Data

US 2006/0041258 A1    Feb. 23, 2006

Related U.S. Application Data

(60) Provisional application No. 60/602,718, filed on Aug. 19, 2004.

(51) Int. Cl.
*A61F 2/44* (2006.01)
(52) U.S. Cl. .................. 623/17.11; 623/17.13
(58) Field of Classification Search .... 623/17.11–17.16; 606/86 R, 86 A, 99, 100; 16/365; 59/79.1, 59/79.3, 80, 35.1; 63/5.1
See application file for complete search history.

(56) References Cited

U.S. PATENT DOCUMENTS

| | | | | |
|---|---|---|---|---|
| 2,245,875 | A | * | 6/1941 | Rutherford .................. 446/487 |
| 3,994,126 | A | * | 11/1976 | Rieth ............................ 59/79.3 |
| 4,239,036 | A | * | 12/1980 | Krieger .......................... 600/206 |
| 4,999,990 | A | * | 3/1991 | Wong ............................ 59/79.1 |
| 5,122,131 | A | | 6/1992 | Tsou |
| 5,171,278 | A | * | 12/1992 | Pisharodi ...................... 128/898 |
| 5,176,678 | A | | 1/1993 | Tsou |
| 5,192,077 | A | * | 3/1993 | Caicedo .......................... 273/155 |
| 5,235,966 | A | * | 8/1993 | Jamner .......................... 600/204 |
| 5,467,763 | A | * | 11/1995 | McMahon et al. ............. 600/201 |
| 5,522,899 | A | * | 6/1996 | Michelson ...................... 606/61 |
| 5,558,665 | A | * | 9/1996 | Kieturakis ......................... 606/1 |
| 5,716,416 | A | | 2/1998 | Lin |
| 5,904,649 | A | * | 5/1999 | Andrese ........................ 600/204 |
| 6,025,538 | A | * | 2/2000 | Yaccarino, III ............... 128/898 |
| 6,039,761 | A | | 3/2000 | Li et al. |
| 6,095,226 | A | * | 8/2000 | Chen et al. ..................... 160/135 |
| 6,206,924 | B1 | * | 3/2001 | Timm ........................ 623/17.16 |
| 6,298,650 | B1 | * | 10/2001 | Amundsen et al. ............... 59/80 |
| 6,368,351 | B1 | | 4/2002 | Glenn et al. |
| 6,387,130 | B1 | | 5/2002 | Stone et al. |
| 6,436,140 | B1 | * | 8/2002 | Liu et al. ..................... 623/17.11 |
| 6,582,451 | B1 | * | 6/2003 | Marucci et al. ................ 606/207 |
| 6,595,998 | B2 | * | 7/2003 | Johnson et al. ................. 606/90 |
| 6,652,584 | B2 | * | 11/2003 | Michelson .................. 623/17.11 |
| 6,705,989 | B2 | * | 3/2004 | Cuschieri et al. .............. 600/208 |
| 2003/0028251 | A1 | * | 2/2003 | Mathews .................... 623/17.16 |
| 2004/0059421 | A1 | | 3/2004 | Glenn et al. |
| 2004/0193158 | A1 | * | 9/2004 | Lim et al. ........................ 606/61 |
| 2005/0055097 | A1 | * | 3/2005 | Grunberg et al. .......... 623/17.11 |
| 2005/0273166 | A1 | * | 12/2005 | Sweeney .................... 623/17.11 |

* cited by examiner

*Primary Examiner* — Eduardo C Robert
*Assistant Examiner* — Steven J Cotroneo
(74) *Attorney, Agent, or Firm* — Carter, DeLuca, Farrell & Schmidt, LLP

(57) ABSTRACT

A support system includes a plurality of support members and a plurality of cross members. The support system is adapted to fit within an access device for insertion into a space between adjacent vertebrae. A plurality of hinges connects each cross member to at least one support member. The support system is movable between a first state and a second state. In the first state, the support system is substantially linear. In the second state, the support system is configurable into one of several geometric shapes. A number of strings may be attached to the support members for transitioning the support system from the first state to the second state.

22 Claims, 11 Drawing Sheets

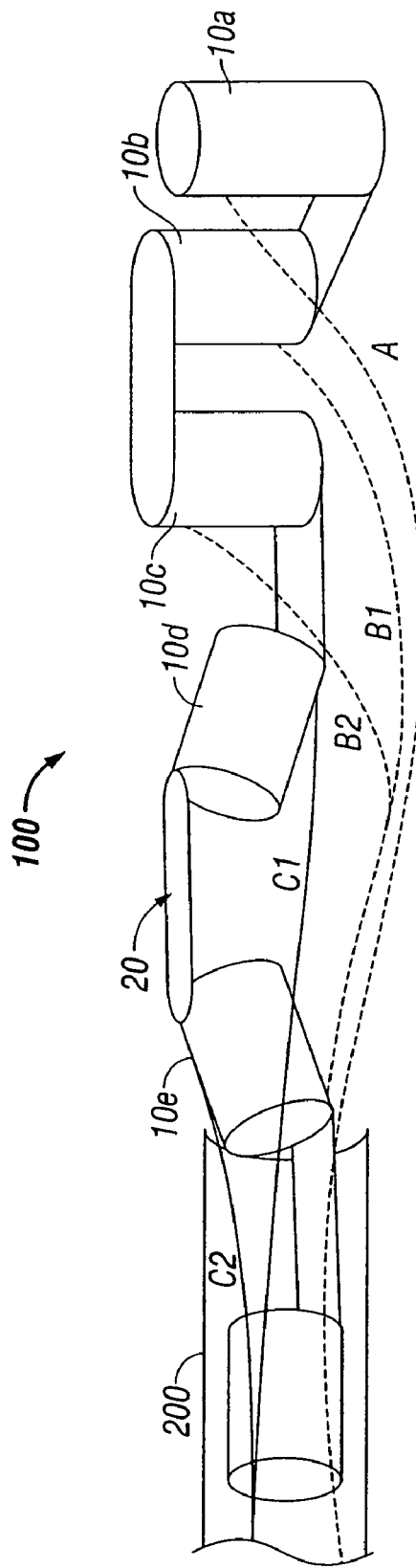
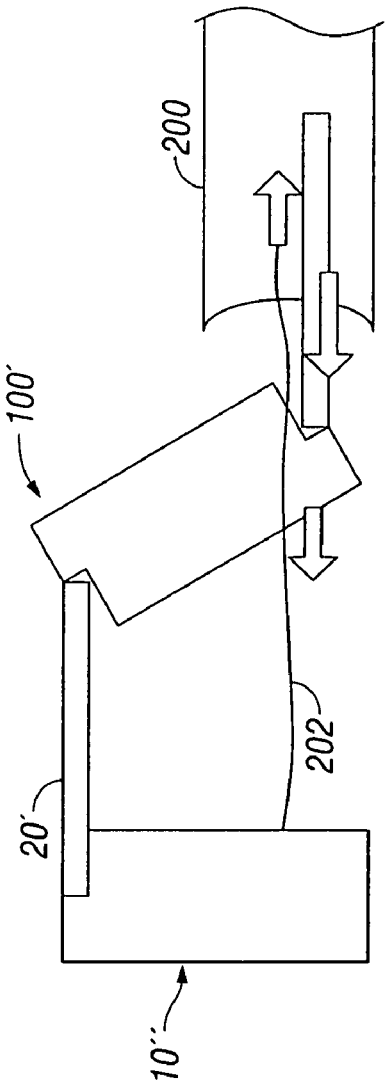
FIG. 7
FIG. 7A

SUPPORT SYSTEM FOR INTERVERTEBRAL FUSION

CROSS-REFERENCE TO RELATED APPLICATIONS

This application claims priority to, and the benefits of, U.S. Provisional Application Ser. No. 60/602,718, filed on Aug. 19, 2004, the entire contents of which are hereby incorporated by reference.

BACKGROUND

1. Technical Field

The present disclosure relates to devices for bone fusion and, more particularly, to a support system for intervertebral fusion.

2. Background of Related Art

Clinicians throughout the developed world recognize the management of low back pain as a widespread problem. Almost three quarters of the U.S. population has at one time experienced low back pain, and about 4% of Americans require surgical intervention in their lifetime, some undergoing multiple procedures. Almost 700,000 spine procedures are performed each year in the United States, and the total cost incurred by back pain and treatment for it exceeds $50 billion per year. Back problems account for almost 30% of workers' compensation claims in the United States. As the population ages, the affected group is growing at about 20% a year.

The number of support systems available for invertebral fusion has grown significantly in the last decade. Cages, inserts, supports, and other devices are commonly implanted between a pair of vertebrae of the spine in order to provide support to the vertebrae and for eventually promoting fusion between the vertebrae. Cages are generally of two types which are rectangular in cross-section or circular in cross-section. Normally, the cages will have windows extending between the top and bottom thereof to allow bone to grow through and fuse together between the vertebrae. Also, the interior of the cage is often packed with bone or other matrix that encourages the growth of bone into the cage and between the two vertebrae and, therefore, a subsequent fusing therebetween.

The shape and insertion method of these support systems vary considerably, with a few even accommodating for some degree of lordosis. Most of the cages are metal, though some are manufactured of a polymer such as polyetheretherketone (PEEK) or other suitable polymers as are known in the art, which is sometimes reinforced with carbon fibers. All the support systems available commercially today have a fixed configuration. Therefore, they are inserted into the body in the same shape as their final form. This fixed configuration of the support systems is a substantial factor in determining the size of the insertion port that is generally at least the same size as the installed support system. Since the vertebral bodies are concave, this requires either a large distraction or the carving of a large access port through the periphery of the vertebrae in order to place the bulky support system at the core of the interbody space. Both of these methods contribute to increased tissue trauma, either to ligaments and musculature in the former case, or to cartilage and vertebrae in the latter. Damage to the ligaments and musculature results in greater postoperative discomfort and a longer healing time, while damage to the vertebral body may cause the implant to fail through subsidence or dislocation.

The need for minimally invasive surgery for spinal procedures has been noted for a number of years. Minimally invasive surgery for implanting traditional prostheses has been shown to reduce intraoperative time while minimizing scarring and postoperative discomfort. These procedures carry with them a unique set of challenges and potential complications, often stemming from the complexity of the method required to implant the device.

Several devices have already been proposed for performing spinal fusion surgery using a procedure that is less invasive than conventional procedures. Some of these devices rely on several separate pieces being placed and assembled in the invertebral space. The others are inserted in a collapsed form and then expanded in the direction of load bearing. Although inserted in a less invasive manner than traditional support systems, both these types of device require considerably wide lateral access to the disc space in order to insert a support system with sufficient surface area to minimize subsidence. Concerns are also raised regarding the mechanical integrity of the devices, essentially whether they will re-collapse in situ.

SUMMARY

The present disclosure is directed towards a support system for use in a minimally invasive or laparoscopic access device. The support system includes a plurality of support members, a plurality of cross members, and a plurality of hinges. Each support member is connected to at least one cross member by one of the hinges. The support system is transitionable between a first or pre-deployed state and a second or deployed state. Additionally, the support system is adapted for insertion into a space defined by adjacent vertebrae.

In its pre-deployed state, the support system extends along a longitudinal axis forming a substantially linear structure and is dimensioned to fit within a laparoscopic access device. Prior to placement in the access device, the support system is dimensioned such that its maximum diameter is substantially equal to the diameter of the support member having the greatest diameter.

The hinges of the support system may be biased towards the deployed state. As such, the bias of each hinge is overcome when the support system is configured in the pre-deployed state. As the support system exits a distal end of the access device, the bias of the hinges causes the support members to transition from a substantially horizontal position to a substantially vertical position (i.e. the deployed state) that is substantially parallel to an axis extending through adjacent vertebrae.

In another embodiment, a plurality of strings is included with the support system to transition it from a pre-deployed (i.e. first) state to a deployed (i.e. second) state. Each string is connected at one end to a portion of a support member while the opposing end of the string is operable from a proximal region of the access device. The strings are attached to the support members and are alternated in their attachment points. A first string may be attached to an end of a support member at a point opposite to its corresponding cross member while a second string is attached to an end of the next support member at a point that is proximate to its corresponding cross member. This arrangement of the attachment points is repeated until all the desired support members are connected to the strings. Sequential movement of the strings, simultaneous movement of the strings, or a combination of sequential and simultaneous movement of the strings causes the support system to transition from the pre-deployed state to the deployed state.

In a further embodiment of the present disclosure, a single string is included with the support system to transition it from a pre-deployed (i.e. first) state to a deployed (i.e. second)

state. Proximal movement of the string transitions the distal-most support member to its second state. As additional support members are located in the workspace, the normal bias of the hinges acts to transition the remaining support members to their second state to form a selected shape of the support system.

Alternatively, a cam and gear mechanism may be adapted for use with support system to transition it from a pre-deployed, state to a deployed state.

In the deployed state, the support system forms a geometric shape. It is envisioned that the deployed support system may be hexagonal, circular, pentagonal, linear, V-shaped, or another shape as required for the specific surgical procedure being performed. In addition, the heights of the support members may not be uniform such that the support system has a height differential between an anterior region and a posterior region. This height differential assists in maintaining a desired degree of lordosis between the adjacent vertebrae.

In one embodiment, a band may be included in the presently disclosed support system. The band is substantially fluid-tight and may be formed from the same material of the support system or another selected biocompatible material. The band substantially circumscribes the support system by forming a barrier wall along an interior or exterior perimeter of the support system. The band may be configured to have a uniform height generally equal to the height of the shortest support member. Alternatively, the band may be configured to have a variable height that conforms to the heights of the support members in the support system. In one embodiment, the band is inserted into the working space after the support system is in its second state and attached thereto to form the barrier wall. In an alternate embodiment, the band is attached to the support system and forms the barrier wall as the support system transitions into the second state. Alternative bone growth materials having fluid or plastic characteristics may be deposited into the working space since the band forms a substantially fluid-tight barrier wall that minimizes the leakage of these alternative materials.

Like conventional support systems, this device separates vertebrae in the spine and maintains proper spacing and structural integrity while the spine heals and fuses through and around the support system. This is needed, for example, in cases where back pain necessitates the removal of a spinal disc. With this device, the procedure can be performed in a minimally invasive or laparoscopic procedure, with all of the attendant benefits that such procedures afford.

BRIEF DESCRIPTION OF THE DRAWINGS

Embodiments of the presently disclosed support system for intervertebral fusion are described herein with reference to the drawings, wherein:

FIG. 7 is a side perspective view of the support system of FIG. 1 including deploying strings and illustrating the transition from its first state to its second state; and FIG. 7A is a side perspective view of the support system of FIG. 1A according to another embodiment of the present disclosure and illustrating the transition from its first state to its second state.

DETAILED DESCRIPTION OF THE PREFERRED EMBODIMENTS

Figure 1:
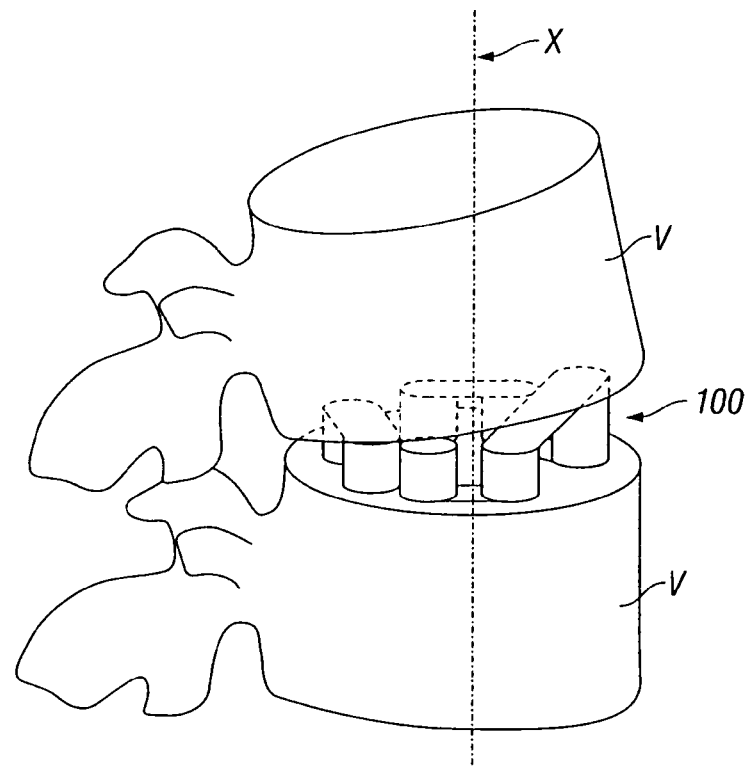
FIG. 1 is a side perspective view of the support system of the present disclosure disposed between adjacent vertebrae.

Embodiments of the presently disclosed support system for intervertebral fusion will now be described in detail with reference to the drawings, in which like reference numerals designate identical or corresponding elements in each of the several views. As used herein, the term "distal" refers to that portion of the instrument, or component thereof which is further from the user while the term "proximal" refers to that portion of the instrument or component thereof which is closer to the user.

Figure 2:
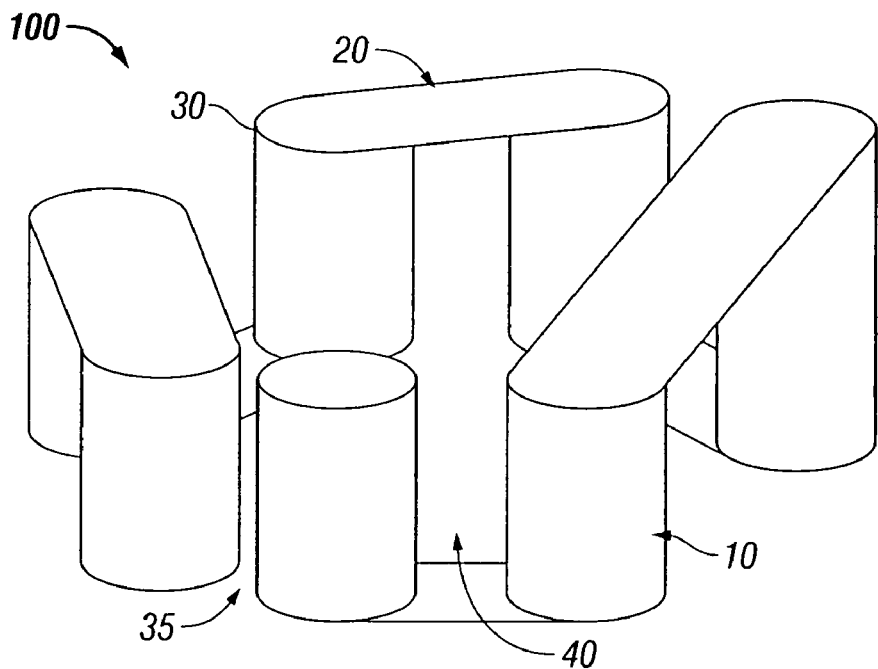
FIG. 2 is a side perspective view of the support system of FIG. 1.
Figure 2A:
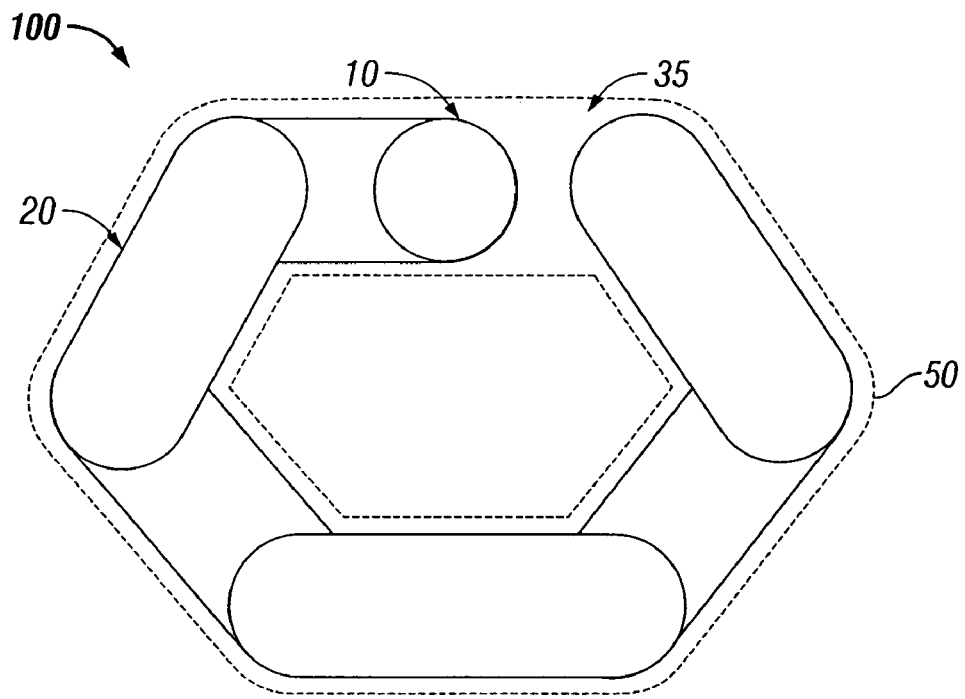
FIG. 2A is a top view of the support system of FIG. 1.
Figure 2B:
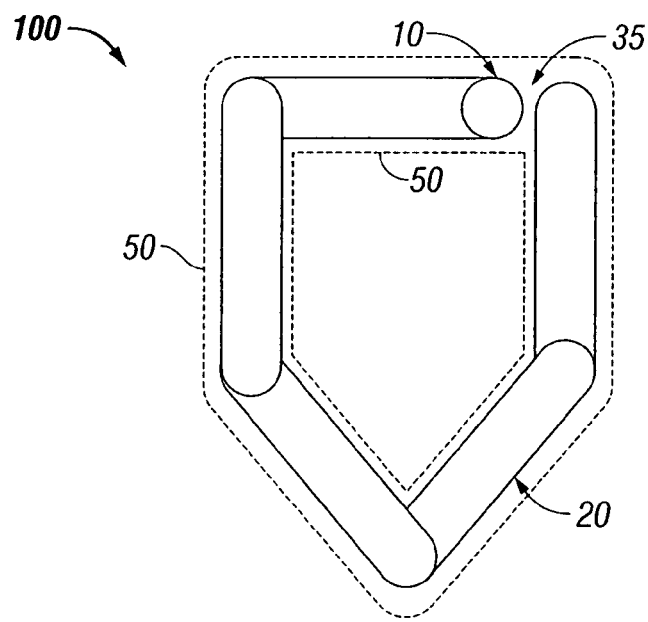
FIG. 2B is a top view of another embodiment of the support system of the present disclosure.
Figure 2C:
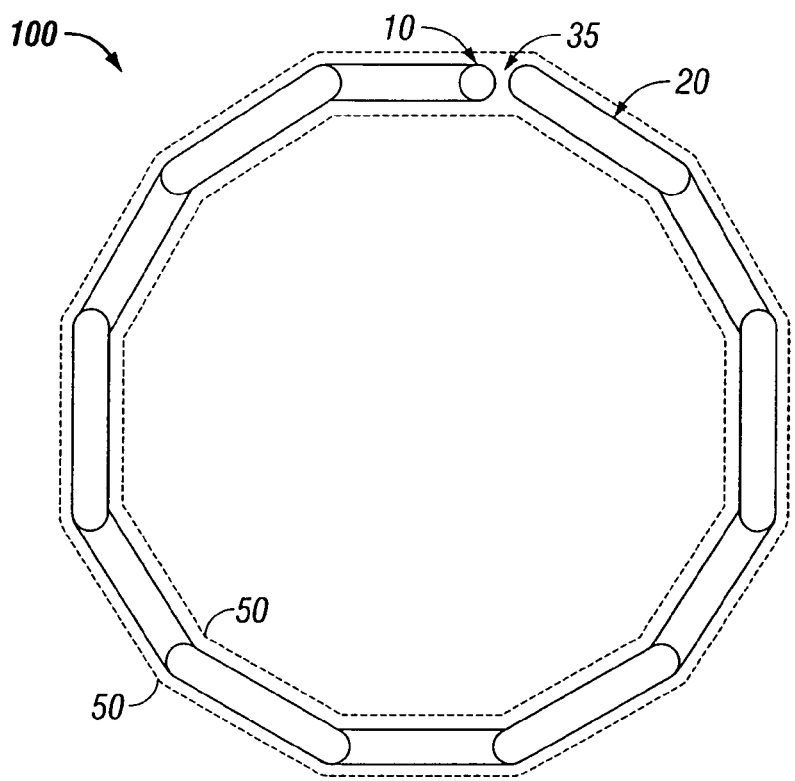
FIG. 2C is a top view of a further embodiment of the support system of the present disclosure.
Figure 2D:
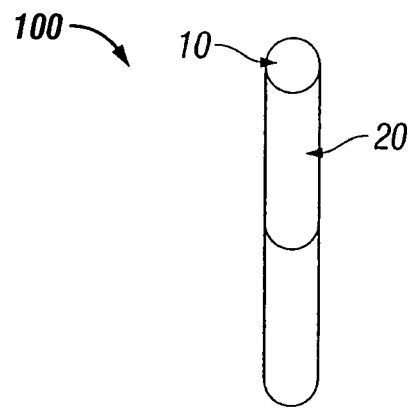
FIG. 2D is a top view of an alternate embodiment of the support system of the present disclosure.
Figure 2E:
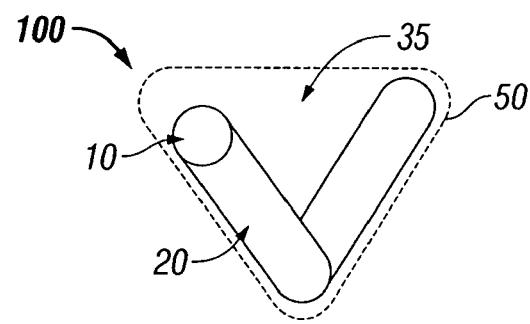
FIG. 2E is a top view of another embodiment of the support system of the present disclosure.
Figure 4:
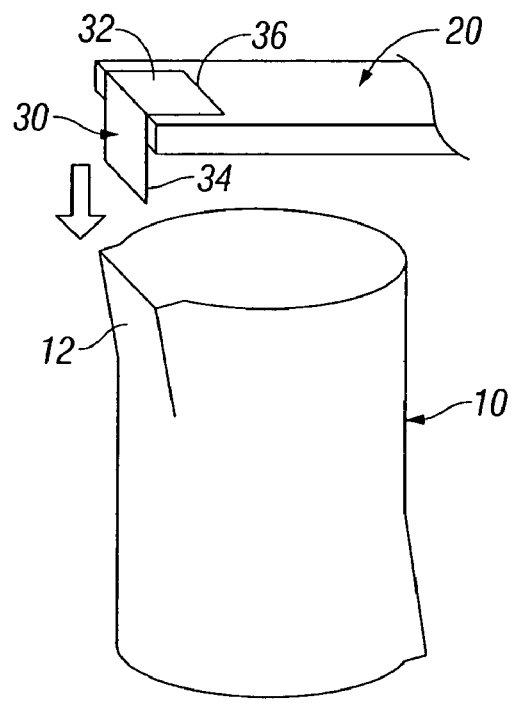
FIG. 4 is a side perspective view of a hinge according to an embodiment of the present disclosure.

A support system 100, in accordance with one embodiment of the present disclosure, is illustrated in FIGS. 1 and 2. Support system 100 includes a plurality of vertical or support members 10 (FIG. 2) and a plurality of horizontal or cross members 20 (FIG. 2), wherein each cross member 20 is attached to a support member 10 using a hinge 30 (FIG. 4). Each support member 10 and each cross member 20 may be a solid structure. In such a configuration, the vertical and cross members 10, 20 may be uniformly formed from a selected material or they may be formed from layers of differing materials. Alternatively, the vertical and cross members 10, 20 may be a hollow structure or define an internal cavity having a number of reinforcing components such as ribs formed from a suitable biocompatible material. It is further contemplated that one or more of the vertical or cross members 10, 20 can include ports or openings adapted for receiving autologous bone, bone growth stimulants, or other bone-growth-promoting medium for facilitating bone growth.

The cross members 20 connect adjacent support members 10 to each other as will be discussed in further detail hereinbelow. In one embodiment, support system 100 is adapted for insertion through an access device 200 having an elongated tubular member (FIG. 6A) smaller than about 8 mm. Suitable access devices for inserting the support system 100 are well known in the art. Alternatively, other sized access devices may be substituted and typically range in size from about 5 mm to about 10 mm in diameter. One possible application for the support system 100 is in posterior invertebral lumbar fusion (PLIF) procedures. The support system 100 can be deployed in situ to its full size including possibly a height differential, measured from a posterior portion to an anterior portion, to accommodate a natural degree of lordosis. In FIG. 1, the support system 100 is illustrated disposed between two adjacent lumbar vertebrae V, thereby maintaining a predetermined amount of vertical spacing and lordosis therebetween. The support system 100 may be made of a polymer such as PEEK. Alternatively, the support system 100 may be formed from other suitable biocompatible materials as are known in the art.

The support members 10 that are not connected to one another by a cross member 20 are spaced apart to define an opening 35, which may be of negligible width. Adjacent support members 10 that are connected by a cross member 20 are spaced apart from one another to define a gap 40. In one embodiment, the opening 35 faces the insertion point and a plurality of gaps 40 along the periphery between the support members 10 allow for the support system 100 to be filled if desired with autologous bone or other bone-growth-promoting medium for fusion to occur.

Generally, the support system 100 provides structural support and maintains the normal invertebral spacing while allowing for bone growth that will eventually fuse the spine and take over the job of bearing the patient's weight. The height of the support system 100 is particularly important, and should accommodate a natural degree of lordosis as shown in FIG. 1. Maintaining the natural spacing and curvature of the spine will result in minimizing stress on the surrounding ligaments and musculature. This in turn will minimize the amount of postoperative discomfort experienced with other devices that do not accommodate a natural amount of lordosis.

Besides accommodating the above requirements for distraction and load bearing, the support system 100 ideally is configured to be inserted through an access device as small as possible as discussed previously. This requires some degree of reconfiguration of current designs in order to collapse the support system 100 for insertion. Device safety after insertion is maximized since the support members 10 of the support system 100 are formed from materials having suitable characteristics and the geometric configuration of the deployed support system 100. The structural configuration for transitioning the support system 100 from a first or pre-deployed state to a second or deployed state should also be chosen so that the device maintains its structural integrity and configuration after placement between adjacent vertebrae in its deployed state. In one embodiment, a single support system 100 is capable of maintaining a desired amount of vertical spacing and lordosis to minimize procedural complexity and allow for easier filling with a bone-growth-promoting material.

The overall geometry of one embodiment of the support system 100 is illustrated in FIG. 2. A natural degree of lordosis is achieved by a combination of incremental support member 10 heights and angles of the cross members 20. Alternately, other degrees of lordosis are achievable by altering the configuration of the support system 100. The support system 100 can be manufactured in several sizes and configurations. In one embodiment, the support system 100 has a height in the range of about 8-12 mm posteriorly and about 10-14 mm anteriorly. In an alternate embodiment, the support system 100 has a height in the range of about 9-11 mm posteriorly and about 11-13 mm anteriorly. In a further embodiment, the support system 100 would have a height of about 10 mm posteriorly and about 12 mm anteriorly. In one embodiment, the support system 100 has a length in the range of about 30-50 mm and a width in the range of about 20-40 mm. In another embodiment, the support system 100 has a length in the range of about 35-45 mm and a width in the range of about 25-35 mm. In a further embodiment, the support system 100 has a length of about 40 mm and a width of about 30 mm. In each of the embodiments, the height differential between the anterior height and the posterior height may be between about 0 mm and about 5 mm.

In applications involving the cervical region, the support system 100 will be substantially circular and generally smaller than support systems 100 used in the lumbar region. By way of example only, the support system 100 may have a length in the range of about 10-20 mm, a width in the range of about 20-40 mm, and a height in the range of about 3-8 mm.

Referring additionally to FIGS. 2A-2E, alternate embodiments of the support system 100 are illustrated. As illustrated, the support system 100 may include three support members 10 (FIG. 2D), thirteen support members 10 (FIG. 2C), or a selected number of support members suitable for the intended procedure. The number of support members 10, cross members 20, and the resulting geometric configuration of the support system 100 is selectable and is influenced by a number of considerations including, but not limited to, the region of the patient's body where the support system 100 is to be installed, the surgical procedure to be conducted, the materials used in forming the support system 100, and the bone growth material selected. The shape of the deployed support system may be hexagonal, circular, pentagonal, linear, V-shaped, or another selected configuration.

A band 50, shown in phantom, may be included with the support system 100. The band 50 is a substantially fluid-tight structure and may be formed from the same material as the support system or another suitable biocompatible material. In one embodiment, the band 50 is extends along an exterior surface of each support member 10. Alternatively, the band 50 may extend along an interior surface of each support member. In either embodiment, the band 50 substantially circumscribes, respectively, the exterior or interior perimeter of the support system 100.

In addition, the band 50 extends vertically for a distance substantially equal to a height of each support member 10 forming a barrier wall that surrounds the support system 100. Alternatively, the band 50 may be formed of a uniform height that is in the range of about the height of the shortest support member 10 to about the height of the tallest support member 10. In either embodiment, the band 50 substantially circumscribes the support system 100 and encloses the opening 35 and each gap 40.

In one embodiment, the band 50 is inserted using the access device 200 after the support system 100 is deployed or may be inserted using a separate access device. A surgical instrument, such as a grasper, may be used to assist in positioning the band 50 in the space created between the adjacent vertebrae. Alternatively, the band 50 may be attached to the support system 100 in a manner such that when the support system 100 is deployed between adjacent vertebrae in the second state, the band 50 forms a barrier wall as described hereinabove.

In embodiments including the band 50, alternate bone growth materials may be introduced into the workspace. By forming a barrier wall using the band 50, the alternate growth materials having fluidic or plastic properties may be inserted into the support system 100 to promote bone growth between the adjacent vertebrae while minimizing the amount of these materials that leak out from the support system 100.

Figure 3:
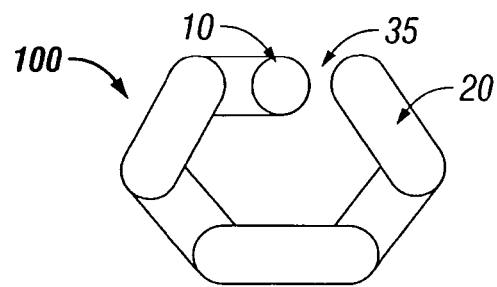
FIG. 3 is a top view of the support system of FIG. 1 in a second state.
Figure 3A:
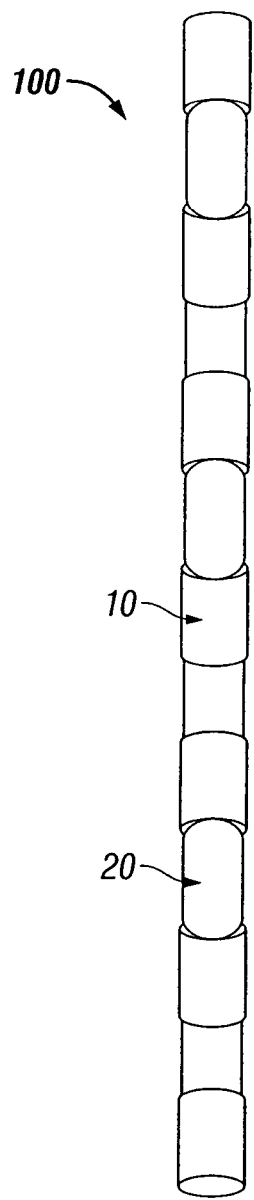
FIG. 3A is a top view of the support system of FIG. 1 in its first state.
Figure 3B:
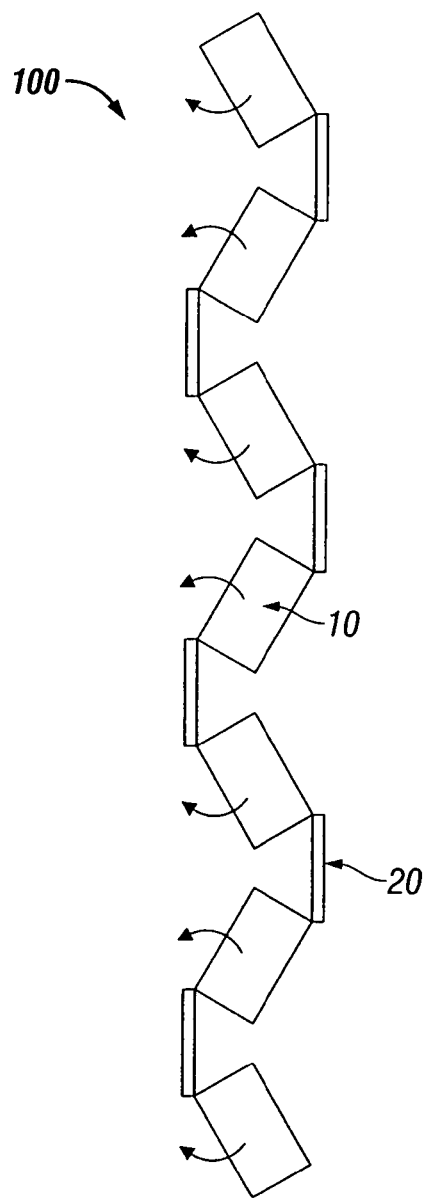
FIG. 3B is a side view of the support system of FIG. 3A in its first state.

In order to collapse the support system 100 for insertion through the access device 200 (FIG. 6A), the support members 10 of the support system 100 are leaned over about a hinge 30 (FIG. 4) at their interface with the cross members 20. By pivoting each support member 10 at the junction of its corresponding hinge 30, the support system 100 is formed into a substantially linear structure (i.e. the first state) configured for insertion through the access device 200, as illustrated in FIG. 3A. In one embodiment, alternate support members 10 lean in opposite directions about a longitudinal axis of the support system 100. This ensures that the support system 100 will not collapse from spinal motion. As each support member 10 is leaned over, it naturally lines up with the support member 10 ahead of it defining a longitudinal axis from a proximal end to a distal end of the support system 100 (FIG. 3A), so that the entire support system 100 can be collapsed to a minimum size of substantially the diameter of the largest support member 10 diameter plus the thickness of the cross member with the greatest thickness. In the pre-deployed state, the support system 100 is substantially linear. The support system 100 is positionable between a first or pre-deployed state (FIG. 3A) and a second or deployed state (FIG. 3). In the second state, support members 10 are substantially parallel with an axis X that extends through adjacent vertebrae (FIG. 1).

Figure 5:
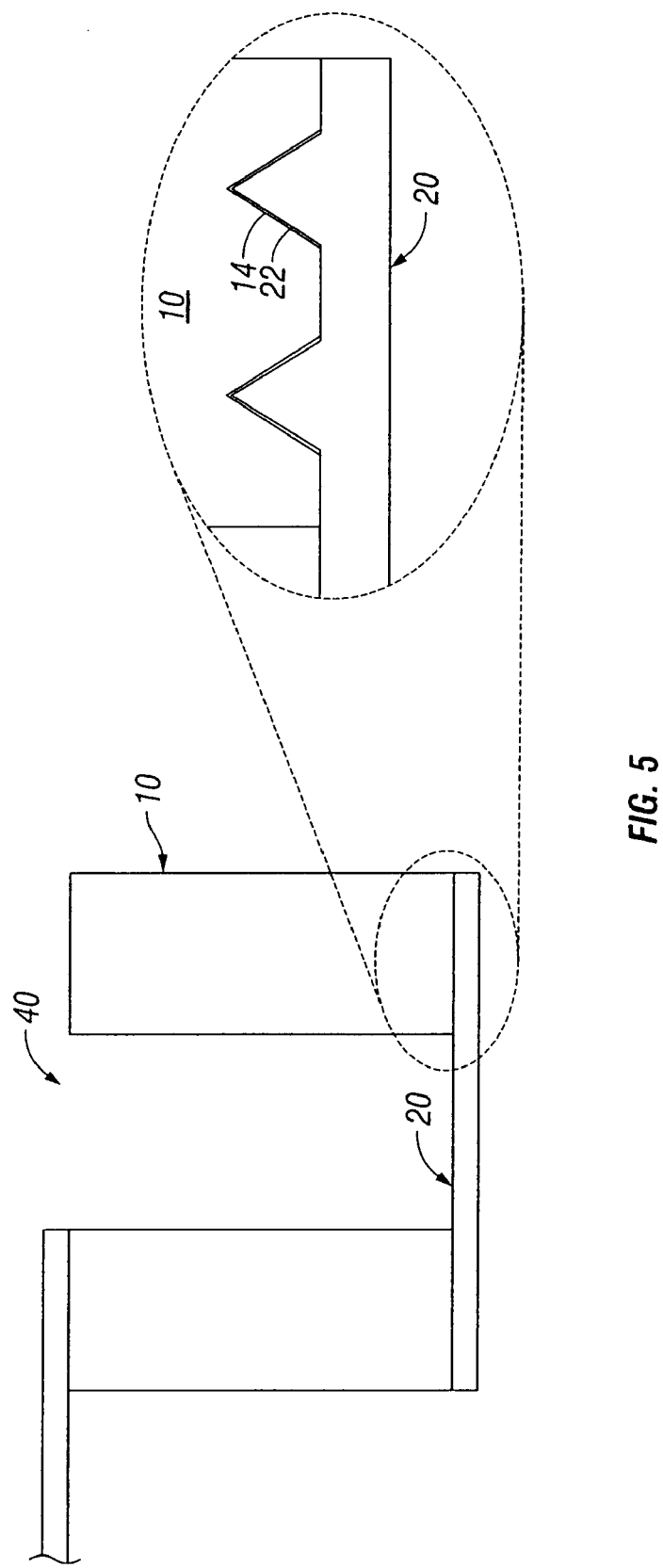
FIG. 5 is a side view of a portion of the support system of FIG. 1 showing a fixation arrangement between a support member and a cross member.

Referring now to FIG. 4, the hinges 30 of the support system 100 do not bear any substantial load in the deployed state. This allows for the use of one of several designs to minimize the dimensions of the hinge 30. In one embodiment, the hinge 30 can be made by fusing a thin layer of a polymer to join the cross member 20 to the support member 10 as illustrated in FIG. 5. Alternatively, the hinge 30 may be formed from reinforced PEEK or another suitable biocompatible material. Hinge 30 allows relative pivotal movement between cross member 20 and support member 10.

Figure 1A:
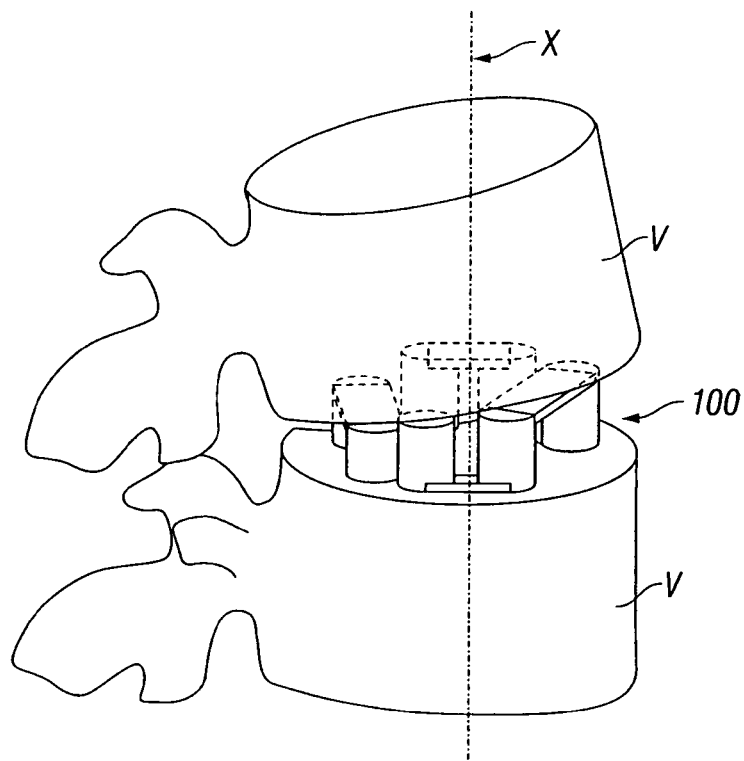
FIG. 1A is a side perspective view of an alternate embodiment of the support system of the present disclosure disposed between adjacent vertebrae.
Figure 4A:
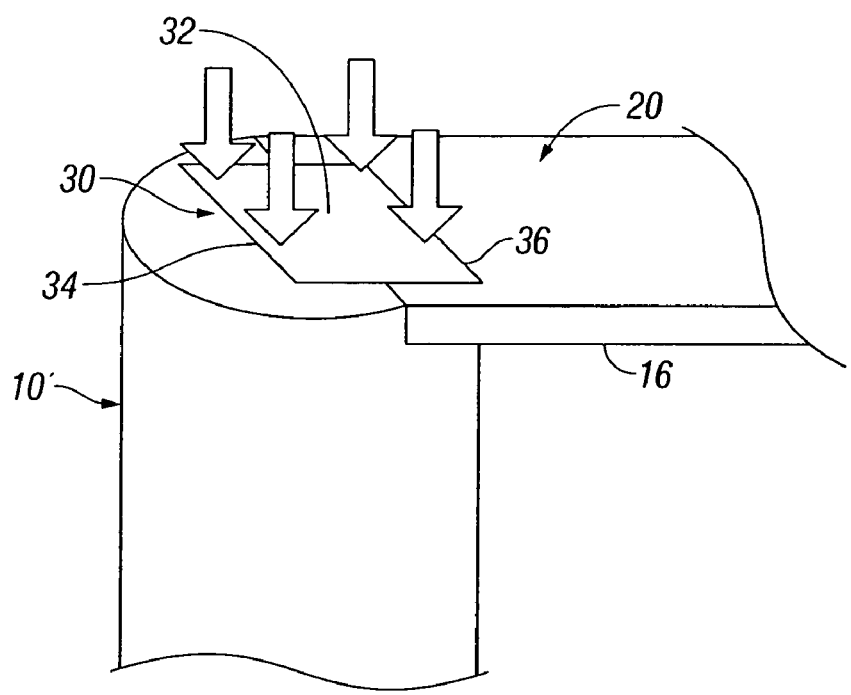
FIG. 4A is a side view of a hinge according to another embodiment of the present disclosure.

In embodiments where both the horizontal members 20 and the vertical members 10 of the support system 100 are made of PEEK, a flexible sheet of PEEK 32, shown shaded for clarity, can be fused at their juncture. The vertical members 10 can be constructed with a flat lip 12 on an appropriate side, so that the hinge 30 is straight, which is the most flexible configuration. When the sheets 32 is fused to the horizontal members 20 and the vertical members 10, the entire support system 100 is bonded chemically so that there are no separate pieces to come apart. Sheet 32 includes a first end 34 and a second end 36, wherein first end 34 is bonded to the flap 12 of the vertical member 10 and the second end 36 is bonded to an end of the horizontal member 20. Alternatively, hinge 30 may be formed by fusing a thin layer of material to support member 10' and cross member 20, as shown in FIG. 4A. As shown in FIG. 4A, support member 10' includes at least one ledge 16 that is recessed below an end surface of support member 10' such that when cross member 20 is attached to support member 10' by hinge 30, a top surface of cross member 20 is substantially coplanar with the top surface of support member 10'. In an embodiment of the present disclosure, the most distal and the most proximal support members 10" include a single ledge while other support members 10" include a pair of opposed ledges 16. In addition, hinge 30 may have a bias that urges cross member 20 towards an orthogonal relationship with support member 10. In the second state, support members 10' and 10" are substantially parallel with an axis X that extends through adjacent vertebrae (FIG. 1A).

Figure 4B:
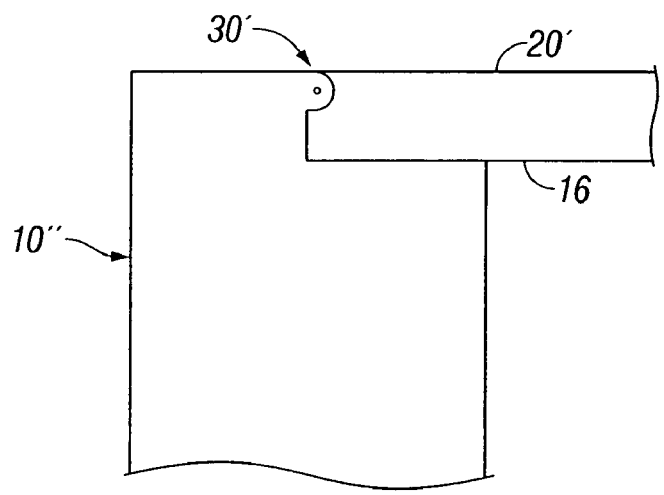
FIG. 4B is a side view of a hinge according to a further embodiment of the present disclosure.
Figure 4C:
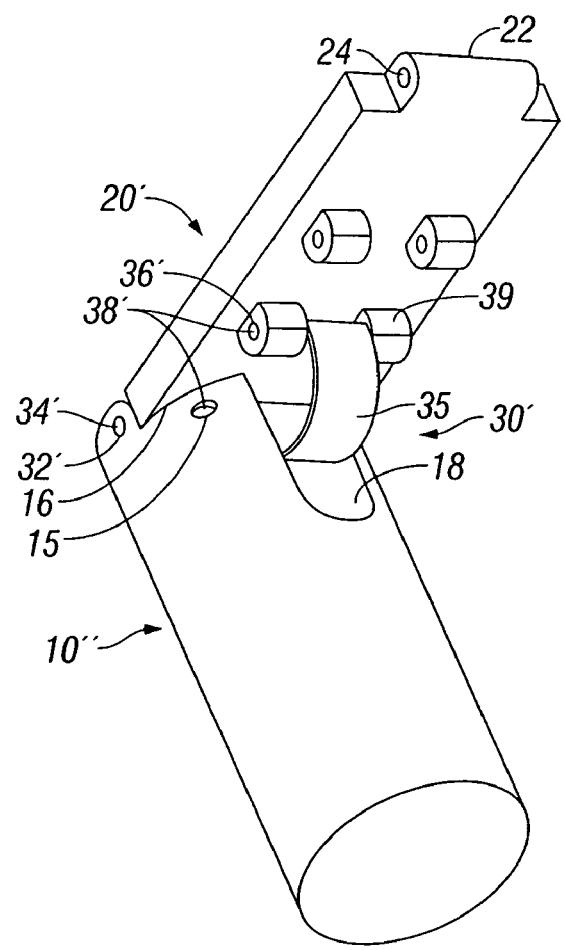
FIG. 4C is a bottom perspective view of the hinge shown in FIG. 4B.

In a further embodiment, as shown in FIGS. 4B and 4C, support member 10" is attached to cross member 20' using a hinge 30'. Support member 10" includes a ledge 16 that is substantially similar to ledge 16 of support member 10' and a cavity 18. A throughbore 32' is located in proximity to ledge 16. A semi-circular extension 22 is located at each end of cross member 20'. Each extension 22 includes a throughhole 24. When cross member 20' is coupled to support member 10" (i.e. positioned on ledge 16), throughbore 32' substantially aligns with throughhole 24, thereby defining a passage therethrough. Once throughbore 32' and throughhole 24 are in substantial alignment, a pin 34' is inserted into the passage and hingedly affixes cross member 20' to support member 10" and allows cross member 20' to be pivoted relative to support member 10".

In addition, cross member 20' includes one or more pairs of semi-circular spindles 39. Each spindle 39 includes an orifice 36' that is adapted for receiving a pin 38' therethrough. In addition, support member 10" includes an opening 15 that is adapted for receiving pin 38'. A biasing member 35 includes openings (not shown) at its opposing ends. It is envisioned that biasing member 35 may be spring that may be fabricated from a suitable metal or other tensile material. One end of biasing member 35 is affixed to support member 10" by inserting pin 38' through openings 15 and the opening in biasing member 35 while the opposing end is affixed to cross member 20' by inserting pin 38' through orifice 36' and the opening in biasing member 35. Biasing member 35 normally biases cross member 20' towards ledge 16 such that it is substantially orthogonal to support member 10" and assists in deployment of support system 100'. In an alternate embodiment, hinge 30' does not include biasing member 35 and provides a pivoting connection between support member 10" and cross member 20'. By providing support system 100' with hinges 30', in its first state (FIG. 3C) support system 100' has a smaller diameter than support system 100, thereby allowing it to be deployed through an access device having a smaller diameter opening. In this embodiment, support system 100' has a diameter that is substantially equal to the diameter of the support member having the greatest diameter. Hinges 30 and 30' are adapted for allowing cross members 20 and 20' to be oriented in a plurality of angles in respect to support members 10, 10', or 10". Within this plurality of angles, cross members 20 and 20' may be substantially orthogonal or substantially coplanar with respect to support members 10, 10', or 10".

The cross members 20 and the support members 10 can have respective pins 22 and notches 14 that mate at their interface in the deployed configuration (FIG. 5). The pins 22 and the notches 14 have complementary configurations and dimensions to maximize their engagement. This additional structural configuration maximizes the structural integrity of the support system 100, thereby minimizing the possibility that the support system 100 will transition from its deployed state to its pre-deployed state after it is placed in the invertebral space. Simply put, support system 100 is adapted and configured to maintain the invertebral space after it transitions from its first state to its second state.

Figure 2F:
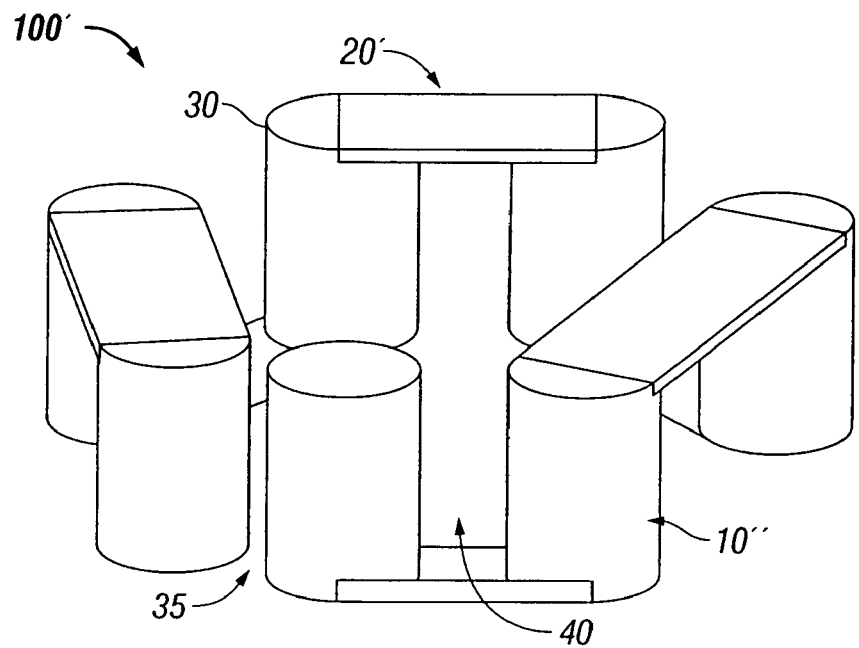
FIG. 2F is a side perspective view of the support system of FIG. 1A.
Figure 3C:
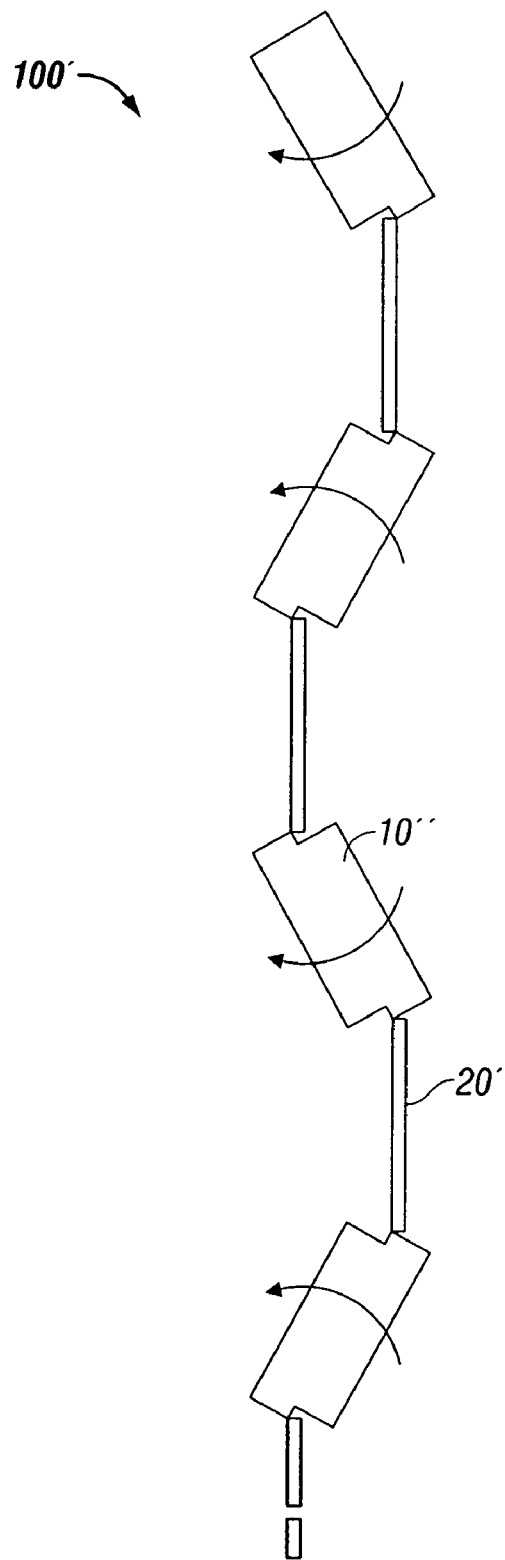
FIG. 3C is a side view of the support system of FIG. 1A in its first state.

In a further embodiment of the present disclosure, support system 100', as illustrated in FIGS. 1A, 2F and 3C, includes a plurality of support members 10″, a plurality of cross members 20′, and a plurality of hinges 30′. Support members 10″, cross members 20′, and hinges 30′ were previously discussed in detail hereinabove and, for the sake of brevity, will not be repeated. Support system 100′ is substantially similar to support system 100.

Further still, with respect to both support systems 100 and 100′, although support members 10, 10′, and 10″ are illustrated as being substantially cylindrical, other shapes (i.e. rectangular or triangular) are equally suitable for use in either support system. In addition, the support member may be fabricated from either a polymer, a metal, or other suitable biocompatible material regardless of the selected shape.

Figure 6C:
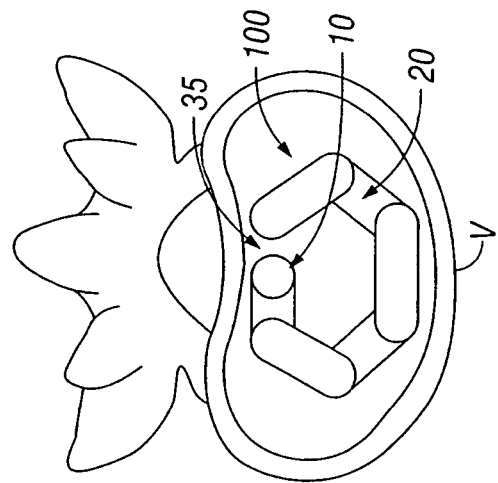
FIG. 6C is a top view of the space above the vertebra showing the support system of FIG. 1 in its second state.
Figure 6B:
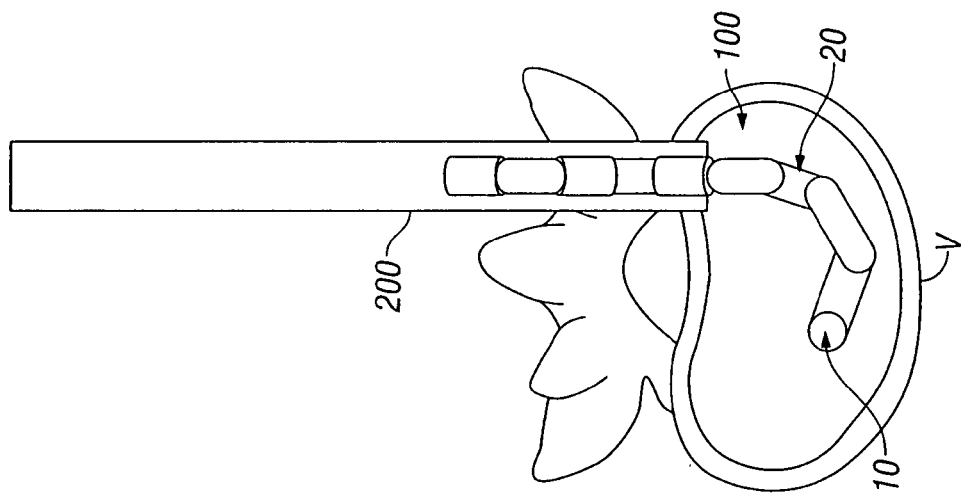
FIG. 6B is top view of a space above the vertebra showing the insertion device in cross-section with the support system of FIG. 1 as the support system is inserted into the space above the vertebra.
Figure 6A:
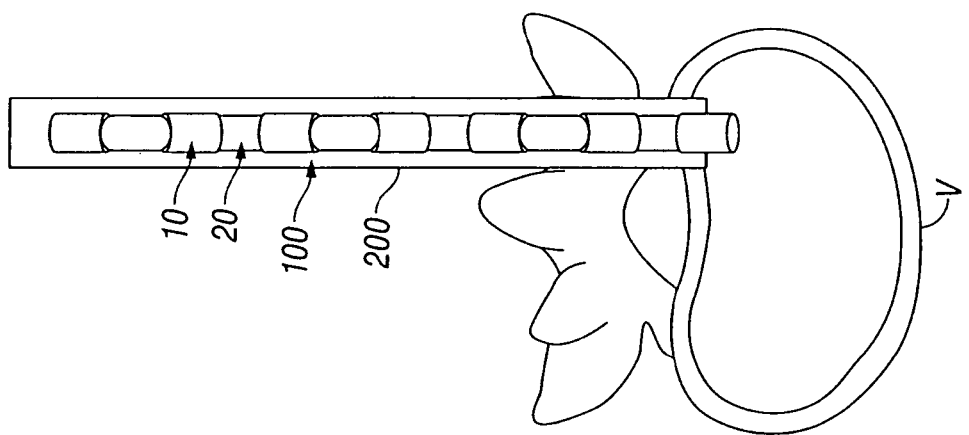
FIG. 6A is top view of a space above a vertebra showing an insertion device in cross-section with the support system of FIG. 1 in its first state.

The insertion and deployment of the support system 100 disclosed herein will be through the access device 200 (FIG. 6A). Although the following discussion and related drawings are directed towards support system 100, support system 100′ may be substituted for support system 100 in any of the embodiments of the present disclosure. Access device 200 may be inserted from a posterior, lateral, or anterior aspect allowing the practitioner to select the point of entry. A small incision is made through which the access device 200. In one embodiment of the disclosure, the access device 200 is no greater than 8 mm in diameter. Once the access device 200 is inserted at the appropriate level, the musculature is dilated until the disc is exposed. Standard procedures are followed to remove the diseased nucleus, leaving the port facing the hollowed portion of the disc.

The support system 100 is inserted through the port in its compact configuration and is deployed in situ. The insertion steps are shown in FIGS. 6A-6C. As the support system 100 is inserted past the end of the access device 200, the support members 10 can stand up one by one or in pairs. A number of structural configurations are adaptable for deploying the support system 100. In one embodiment, the hinges 30 may be biased towards the deployed state. Prior to deployment, the support system 100 is stored in the access device 200 in its pre-deployed state that overcomes the biasing of the hinges 40. As portions of the support system 100 exit the distal end of the access device 200, the biasing of the hinges 30 act to pull the support system 100 into position by moving the support members 10 from a substantially horizontal position (FIG. 6A) to a substantially vertical position (FIG. 6C). Support system 100 has sufficient rigidity such that a distally directed force applied to surgical system 100 urges support members 10 and cross members 20 distally through a lumen in access device 200.

In a further embodiment, as shown in FIG. 7, strings may attached to each support member 10 on the side facing the rear of the access device 200, at the end inserted first. The strings are paired according to the top cross members 20. For example, in FIG. 7, the first support member 10a inserted is deployed by pulling on string A. The next two support members 10b, 10c are deployed by pulling on strings B1 and B2. They can be deployed independently or together. In the configuration of FIG. 7, support members 10d, 10e are awaiting deployment, which will be achieved by pulling on strings C1 and C2. As each support member 10 is moved to a substantially vertical position, the carefully angled and/or biased hinges 30 automatically bend the support system 100 to its deployed shape.

Once the support system 100 is deployed, the strings are cut and pulled free. The support system 100 can then be packed with bone graft or other bone-growth-promoting material, and the annulus stitched shut if desired.

Alternatively, support system 100′ may be deployed using a single string 202 in connection with access device 200, as shown in FIG. 7A. In this embodiment, string 202 is attached to a portion of the distalmost support member 10″. When the distalmost support member 10″ is positioned in the workspace, string 202 is repositioned towards the user (i.e. proximally) such that the distalmost support member 10″ transitions from its first state to its second state (i.e. substantially upright). As additional support members 10″ are positioned in the workspace, biasing members 35 urge support members 10″ to transition from their first state to their second state. As each support member 10″ is moved to a substantially vertical position, hinges 30′ automatically bend the support system 100′ to its deployed shape.

Another method is to employ a cam-and-gear mechanism operable from the proximal or surgeon's end of the access device to deploy the members as they are inserted. A combination of these devices can also be used.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. An apparatus comprising:
 a plurality of support members;
 a plurality of cross members, each cross member in the plurality of cross members connecting adjacent support members, wherein the support members are repositionable from a first state to a second state, the support members being substantially collinear with respect to the other support members in the first state, each cross member being substantially parallel with respect to the other cross members in the first state, and the support members and the cross members defining a substantially orthogonal relationship therebetween in the second state, wherein a space is defined between a surface of at least one support member and its respective cross member when the apparatus is in the first state and the surface of the at least one support member and at least a part of a surface of its respective cross member are in contact with each other when the apparatus is in the second state; and
 a plurality of hinges, each hinge in the plurality of hinges coupling its respective support member to its respective cross member, and each hinge includes a biasing member that urges the cross members towards a substantially orthogonal relationship with the support members in the second state of the apparatus, wherein the plurality of support members pivot relative to a longitudinal axis of the apparatus such that the plurality of support members are substantially parallel to an axis extending through adjacent vertebrae, thereby defining the second state of the apparatus.

2. The apparatus of claim 1, wherein the apparatus is disposed in an access device.

3. The apparatus of claim 2, wherein at least one string is attached to at least one support member and proximal movement of the string transitions the apparatus from the first state to the second state.

4. The apparatus of claim 2, wherein the access device has a diameter of between about 5 mm and about 10 mm.

5. The apparatus of claim 1, wherein the first state of the apparatus defines a shape selected from the group consisting of: hexagonal, circular, pentagonal, linear, or V-shaped.

6. The apparatus of claim 1, wherein the second state of the apparatus is capable of maintaining a gap between adjacent vertebrae and defining a working space therebetween.

7. The apparatus of claim 1, wherein the support members are parallel to each other when the apparatus is in the second state.

8. The apparatus of claim 7, wherein the cross members are parallel to each other when the apparatus is in the second state.

9. A method of maintaining an intervertebral space between adjacent vertebrae, comprising the steps of:
providing a surgical apparatus having a plurality of support members with a plurality of hinges that couple the plurality of support members to a plurality of cross members, wherein the support members pivot relative to a longitudinal axis of the apparatus thereby transitioning from a first state to a second state, the support members and the cross members being substantially colinear in the first state, the support members and the cross members defining a substantially orthogonal relationship therebetween in the second state, wherein the plurality of support members are substantially parallel to an axis extending through adjacent vertebrae, thereby defining the second state of the apparatus and the support members are spaced apart defining a plurality of gaps therebetween such that the apparatus has an alternating arrangement of support members and cross members in the first state and in the second state, wherein each of the gaps has a length that is substantially defined by the length of the cross member;
inserting an access device through an incision of a patient, wherein the access device includes the surgical apparatus such that the support members and the cross members are substantially colinear and define a first state of the surgical apparatus;
positioning the access device within the intervertebral space;
deploying the surgical apparatus; and
transitioning the surgical apparatus from the first state to the second state.

10. The method of claim 9, wherein the hinges include a biasing member that urges the cross members towards a substantially orthogonal relationship between the plurality of support members and the axis.

11. The method of claim 9, wherein the step of transitioning the surgical apparatus includes the step of:
moving at least one string connected to at least one support member.

12. The method of claim 9, wherein the second state of the surgical apparatus defines a shape selected from the group consisting of: hexagonal, circular, pentagonal, linear, or V-shaped.

13. The method of claim 9, wherein the second state of the apparatus is capable of maintaining a gap between adjacent vertebrae and defining a working space therebetween.

14. The method of claim 9, further comprising the step of:
adding a quantity of a bone growth material to the working space.

15. An apparatus comprising:
a plurality of support members;
a plurality of cross members, each cross member in the plurality of cross members connecting adjacent support members, wherein the support members are repositionable from a first state to a second state, the support members being substantially collinear with respect to the other support members in the first state, the cross members being substantially parallel with respect to the other cross members in the first state, and the support members and the cross members defining a substantially orthogonal relationship therebetween in the second state, wherein a space is defined between a surface of at least one support member and its respective cross member when the apparatus is in the first state and the surface of the at least one support member and at least a part of a surface of its respective cross member are in contact with each other when the apparatus is in the second state, wherein the support members are spaced apart defining a plurality of gaps therebetween such that the apparatus has an alternating arrangement of support members and cross members in the first state and in the second state, wherein each of the gaps has a length that is substantially defined by the length of the cross member; and
a plurality of hinges, each hinge in the plurality of hinges coupling its respective support member to its respective cross member, wherein the plurality of support members pivot relative to a longitudinal axis of the apparatus such that the plurality of support members are substantially parallel to an axis extending through adjacent vertebrae, thereby defining the second state of the apparatus.

16. The apparatus of claim 15, wherein at least one string is attached to at least one support member and proximal movement of the string transitions the apparatus from the first state to the second state.

17. The apparatus of claim 15, wherein the second state of the apparatus is capable of maintaining a gap between adjacent vertebrae and defining a working space therebetween.

18. The apparatus of claim 15, wherein each hinge includes a biasing member that urges the cross members towards a substantially orthogonal relationship with the support members in the second state of the apparatus.

19. An implantable surgical device comprising:
a plurality of support members;
at least one cross member, the at least one cross member being a planar member and connecting adjacent support members; and
a plurality of hinges, each hinge coupling its respective support member to the at least one cross member such that the device is transitionable between a first state and a second state, the first state defined by the support members being substantially collinear with respect to the other support members, and the second state defined by each support member being parallel with respect to the other support members and orthogonal to the at least one cross member, wherein a space is defined between a surface of at least one support member and its respective cross member when the device is in the first state and the surface of the at least one support member and at least a part of a surface of its respective cross member are in contact with each other when the apparatus is in the second state, wherein a space exists between adjacent support members such that the apparatus has an alternating arrangement of support members and cross members in the first state and in the second state.

20. The device of claim 19, wherein the device includes a plurality of cross members that are parallel to each other as the device transitions from the first state to the second state.

21. The apparatus of claim 19, wherein the second state of the apparatus is capable of maintaining a gap between adjacent vertebrae and defining a working space therebetween.

22. The apparatus of claim 19, wherein at least one string is attached to at least one support member and proximal movement of the string transitions the apparatus from the first state to the second state.

* * * * *